US010598773B2

(12) United States Patent
Sapozhnikov et al.

(10) Patent No.: US 10,598,773 B2
(45) Date of Patent: Mar. 24, 2020

(54) SYSTEMS AND METHODS FOR MEASURING PRESSURE DISTRIBUTIONS OF ACOUSTIC BEAMS FROM ULTRASOUND SOURCES

(71) Applicant: University of Washington, Seattle, WA (US)

(72) Inventors: Oleg A. Sapozhnikov, Seattle, WA (US); Wayne Kreider, Seattle, WA (US); Adam D. Maxwell, Seattle, WA (US); Vera Khokhlova, Seattle, WA (US)

(73) Assignee: University of Washington, Seattle, WA (US)

( * ) Notice: Subject to any disclaimer, the term of this patent is extended or adjusted under 35 U.S.C. 154(b) by 208 days.

(21) Appl. No.: 15/446,923

(22) Filed: Mar. 1, 2017

(65) Prior Publication Data

US 2017/0254887 A1    Sep. 7, 2017

Related U.S. Application Data

(60) Provisional application No. 62/302,293, filed on Mar. 2, 2016.

(51) Int. Cl.
*G03H 3/00*        (2006.01)
*G01S 7/52*        (2006.01)
(Continued)

(52) U.S. Cl.
CPC .............. *G01S 7/5205* (2013.01); *A61B 8/58* (2013.01); *G01S 15/899* (2013.01);
(Continued)

(58) Field of Classification Search
None
See application file for complete search history.

(56) References Cited

U.S. PATENT DOCUMENTS 3,585,847 A  *  6/1971  Brenden .............. A61B 8/0825
                                                                359/900
3,600,935 A  *  8/1971  Baum ....................... A61B 8/00
                                                                359/901

(Continued)

FOREIGN PATENT DOCUMENTS

JP    2006026040       *   2/2006    ............... A61B 8/00
WO   2004031802 A1       4/2004

OTHER PUBLICATIONS

Greguss, Pal, and H. J. Caulfield. "Multiplexing Ultrasonic Wave Fronts by Holography." Science 177.4047 (1972): 422-424. (Year: 1972).*

(Continued)

*Primary Examiner* — Hovhannes Baghdasaryan
*Assistant Examiner* — Jonathan D Armstrong
(74) *Attorney, Agent, or Firm* — Perkins Coie LLP

(57) ABSTRACT

The present technology relates generally to receiving arrays to measure a characteristic of an acoustic beam and associated systems and methods. The receiving arrays can include elongated elements having at least one dimension, such as a length, that is larger than a width of an emitted acoustic beam and another dimension, such as a width, that is smaller than half of a characteristic wavelength of an ultrasound wave. The elongated elements can be configured to capture waveform measurements of the beam based on a characteristic of the emitted acoustic beam as the acoustic beam crosses a plane of the array, such as a transverse plane. The methods include measuring at least one characteristic of an ultrasound source using an array-based acoustic holography system and defining a measured hologram at the array surface based, at least in part, on the waveform measurements. The measured hologram can be processed to reconstruct a characteristic of the ultrasound source. The ultra- (Continued)

sound source can be calibrated and/or re-calibrated based on the characteristic.

23 Claims, 9 Drawing Sheets

(51) Int. Cl.
   *G01S 15/89* (2006.01)
   *A61B 8/00* (2006.01)
   *A61N 7/00* (2006.01)
   *A61N 7/02* (2006.01)
(52) U.S. Cl.
   CPC ............ *G01S 15/8918* (2013.01); *A61N 7/02* (2013.01); *A61N 2007/0078* (2013.01)

(56) References Cited

U.S. PATENT DOCUMENTS

| | | | | |
|---|---|---|---|---|
| 3,685,051 A * | 8/1972 | Wells | G01H 3/125 | 342/179 |
| 3,745,814 A * | 7/1973 | Gabor | A61B 8/0825 | 359/901 |
| 3,765,403 A * | 10/1973 | Brenden | A61B 8/0825 | 128/915 |
| 3,802,533 A * | 4/1974 | Brenden | A61B 8/0825 | 181/176 |
| 3,809,873 A * | 5/1974 | Klahr | G01S 13/9005 | 359/560 |
| 3,919,881 A * | 11/1975 | Metherell | G01N 29/0663 | 359/10 |
| 3,940,619 A * | 2/1976 | Ellingson | A61B 6/00 | 378/23 |
| 3,983,529 A * | 9/1976 | Langlois | G01H 9/002 | 367/10 |
| 4,023,175 A * | 5/1977 | Brown | G01S 13/89 | 342/135 |
| 4,093,382 A * | 6/1978 | Kurtz | G01H 9/002 | 356/72 |
| 4,182,316 A * | 1/1980 | Nilsson | A61B 5/0456 | 600/476 |
| 4,650,302 A * | 3/1987 | Grant | A61B 3/1225 | 351/206 |
| 4,662,730 A * | 5/1987 | Outwater | A61B 3/1225 | 351/212 |
| 4,876,725 A * | 10/1989 | Tomko | A61B 5/1172 | 382/126 |
| 4,948,258 A * | 8/1990 | Caimi | G01B 11/2441 | 356/3.13 |
| 5,070,879 A | 12/1991 | Herres | | |
| 5,115,497 A * | 5/1992 | Bergman | G01S 17/88 | 712/200 |
| 5,164,750 A * | 11/1992 | Adachi | A61B 3/107 | 351/212 |
| 5,177,802 A * | 1/1993 | Fujimoto | A61B 5/1172 | 356/71 |
| 5,202,742 A * | 4/1993 | Frank | G01S 7/4811 | 180/167 |
| 5,243,367 A * | 9/1993 | Spellitz | G01B 11/255 | 351/212 |
| 5,740,806 A | 4/1998 | Miller | | |
| 6,118,119 A * | 9/2000 | Ruschin | G01J 3/0259 | 250/237 G |
| 6,323,949 B1 * | 11/2001 | Lading | G01P 3/366 | 356/28.5 |
| 6,401,540 B1 * | 6/2002 | Deason | G01H 9/00 | 73/657 |
| 6,552,841 B1 * | 4/2003 | Lasser | G01N 29/0609 | 359/305 |
| 6,782,122 B1 * | 8/2004 | Kline | G01F 23/292 | 250/223 B |
| 7,617,732 B2 | 11/2009 | Bui et al. | | |
| 7,796,271 B2 * | 9/2010 | Reithinger | A61B 5/1075 | 356/457 |
| 9,220,478 B2 | 12/2015 | Smith et al. | | |
| 2002/0001110 A1 * | 1/2002 | Metz | A61B 5/1172 | 359/10 |
| 2002/0014533 A1 * | 2/2002 | Zhu | B82Y 15/00 | 235/472.01 |
| 2002/0044279 A1 * | 4/2002 | Khoury | G01J 3/28 | 356/300 |
| 2002/0045819 A1 * | 4/2002 | Garlick | A61B 8/0825 | 600/437 |
| 2002/0111546 A1 * | 8/2002 | Cook | A61B 5/0059 | 600/322 |
| 2002/0161357 A1 * | 10/2002 | Anderson | A61B 18/203 | 606/9 |
| 2003/0020975 A1 * | 1/2003 | Metz | G02B 5/32 | 359/15 |
| 2004/0260159 A1 * | 12/2004 | Gerlitz | A61B 5/14532 | 600/319 |
| 2005/0057684 A1 * | 3/2005 | Tamakoshi | A61B 90/36 | 348/375 |
| 2006/0004306 A1 * | 1/2006 | Altshuler | A61B 18/203 | 601/3 |
| 2006/0270929 A1 * | 11/2006 | Bouma | G01N 21/4795 | 600/407 |
| 2008/0132886 A1 * | 6/2008 | Cohen | A61B 18/203 | 606/34 |
| 2008/0228074 A1 | 9/2008 | Ketterling | | |
| 2008/0297360 A1 * | 12/2008 | Knox | G01N 21/49 | 340/628 |
| 2009/0015923 A1 * | 1/2009 | Auld | A61B 18/22 | 359/566 |
| 2009/0201490 A1 * | 8/2009 | Gerlitz | A61B 5/14532 | 356/39 |
| 2009/0204366 A1 * | 8/2009 | Gerlitz | A61B 5/14532 | 702/179 |
| 2010/0045571 A1 * | 2/2010 | Yamamoto | G02B 27/0172 | 345/8 |
| 2010/0045933 A1 * | 2/2010 | Eberl | A61B 3/113 | 351/210 |
| 2010/0149315 A1 * | 6/2010 | Qu | A61B 1/00193 | 348/46 |
| 2010/0208050 A1 * | 8/2010 | Wadman | A61B 5/0059 | 348/77 |
| 2010/0256488 A1 | 10/2010 | Kim et al. | | |
| 2010/0324373 A1 * | 12/2010 | Lei | A61B 1/00096 | 600/176 |
| 2011/0222068 A1 * | 9/2011 | Heng | G02B 26/06 | 356/457 |
| 2011/0299557 A1 * | 12/2011 | Fairneny | A61B 18/22 | 372/6 |
| 2012/0188509 A1 * | 7/2012 | Hogan | A61B 3/102 | 351/206 |
| 2013/0201798 A1 | 8/2013 | Jensen et al. | | |
| 2015/0103140 A1 * | 4/2015 | Kostuk | A61B 1/00163 | 348/40 |
| 2016/0073853 A1 * | 3/2016 | Venkatesan | A61B 1/0607 | 348/68 |
| 2016/0266242 A1 * | 9/2016 | Gilliland | G01S 7/4814 | |
| 2017/0106204 A1 * | 4/2017 | Segev | A61N 5/0601 | |
| 2017/0242398 A1 * | 8/2017 | Brooker | G02B 21/0056 | |
| 2017/0254887 A1 * | 9/2017 | Sapozhnikov | G01S 15/8918 | |
| 2018/0154029 A1 * | 6/2018 | Shr | A61L 2/10 | |
| 2018/0206723 A1 * | 7/2018 | Zhang | A61B 34/35 | |

OTHER PUBLICATIONS

Sapozhnikov, Oleg A., Andrey V. Morozov, and Dominique Cathignol. "Piezoelectric transducer surface vibration characterization using acoustic holography and laser vibronnetry." Ultrasonics Symposium, 2004 IEEE. vol. 1. IEEE, 2004. (Year: 2004).*

Sapozhnikov, O. A., A. E. Ponomarev, and M. A. Smagin. "Transient acoustic holography for reconstructing the particle velocity of the surface of an acoustic transducer." Acoustical Physics 52.3 (2006): 324-330. (Year: 2006).*

(56) References Cited

OTHER PUBLICATIONS

Tsysar, Sergey A., and Oleg A. Sapozhnikov. "Ultrasonic holography of 3D objects." Ultrasonics Symposium (IUS), 2009 IEEE International. IEEE, 2009. (Year: 2009).*

Tsysar, S. A., Y. D. Sinelnikov, and O. A. Sapozhnikov. "Characterization of cylindrical ultrasonic transducers using acoustic holography." Acoustical Physics 57.1 (2011): 94-105. (Year: 2011).*

Kreider, Wayne, et al. "Characterization of a multi-element clinical HIFU system using acoustic holography and nonlinear modeling." IEEE transactions on ultrasonics, ferroelectrics, and frequency control 60.8 (2013): 1683. (Year: 2013).*

Tsysar, Sergey, Wayne Kreider, and Oleg Sapozhnikov. "Improved hydrophone calibration by combining acoustic holography with the radiation force balance measurements." Proceedings of Meetings on Acoustics ICA2013. vol. 19. No. 1. ASA, 2013. (Year: 2013).*

Sapozhnikov, Oleg A., et al. "Acoustic holography as a metrological tool for characterizing medical ultrasound sources and fields." The Journal of the Acoustical Society of America 138.3 (2015): 1515-1532. (Year: 2015).*

Rosnitskiy, Pavel B., et al. "Design of HIFU transducers for generating specified nonlinear ultrasound fields." IEEE transactions on ultrasonics, ferroelectrics, and frequency control 64.2 (2017): 374-390. (Year: 2017).*

Buma, T. et al., "One-dimensional ultrasound receive array using spectrally encoded optical detection." Applied Physics Letters, vol. 85, No. 24, Dec. 13, 2004, 4 pages.

Sapozhnikov, O.A. et al., "Acoustic holography as a metrological tool for characterizing medical ultrasound sources and fields." J. Accoust. Soc. Am. 138(3), Sep. 2015, 18 pages.

Shu, Y. et al., "One-dimensional Optoacoustic Receive Array Employing Chirped Excitation and GPU-based Beamforming." IEEE, 2011, 4 pages.

Shu, Y. et al., "One-dimensional Optoacoustic Receive Array Employing Parallel Detection and Video-rate Acquisition." IEEE, 2010, 4 pages.

\* cited by examiner

SYSTEMS AND METHODS FOR MEASURING PRESSURE DISTRIBUTIONS OF ACOUSTIC BEAMS FROM ULTRASOUND SOURCES

CROSS-REFERENCE TO RELATED APPLICATION(S)

This application claims the benefit of U.S. Provisional Application No. 62/302,293 filed Mar. 2, 2016, which is herein incorporated by reference in its entirety.

STATEMENT REGARDING FEDERALLY SPONSORED RESEARCH

This invention was made with government support under Grant Nos. R01EB007643 and R21EB016118, awarded by the National Institutes of Health. The government has certain rights in the invention.

TECHNICAL FIELD

The present technology relates generally to receiving arrays, such as one-dimensional receiving arrays, for measuring lateral pressure distribution of acoustic beams emitted by ultrasound sources.

BACKGROUND

High intensity focused ultrasound ("HIFU") is a rapidly developing medical technology that relies on focusing acoustic waves to treat remote tissue sites inside the body without damaging intervening tissues. HIFU can be used to treat benign and malignant tumors, dissolve blood clots, enhance drug delivery to specific sites, and ablate brain tissue causing essential tremors. A key feature of HIFU is the ability to maintain a very thin margin between treated and untreated tissue. However, the position and extent of treatment can be sensitive to many factors, including blood perfusion, tissue properties, and nonlinear acoustic propagation. In order to ensure effective treatments and to avoid adverse effects from unintended tissue injury, it is necessary to accurately determine the three-dimensional acoustic field that will be delivered to the patient. While standard practices for characterizing diagnostic ultrasound are well established, the lack of analogous metrology techniques for therapeutic ultrasound remains an impediment to broader clinical acceptance of HIFU.

Because ultrasound consists of waves, it possesses several basic features of wave physics that are of practical utility. In particular, it is possible to reproduce a three-dimensional field from a two-dimensional distribution of the wave amplitude and phase along some surface transverse to the wave propagation. This principle is widely used in optics, and the corresponding process is termed "holography." A similar approach is possible in acoustics. For acoustic pressure waves, amplitude and phase can often be measured directly with a pressure sensor, and a two-dimensional distribution of such measurements represents a hologram.

Mathematically, the hologram provides a boundary condition for the wave equation, thereby permitting the calculation of acoustic variables anywhere in three-dimensional space, including the surface of the ultrasound transducer itself. However, it can be difficult to characterize an acoustic field created by a given ultrasound transducer with a high degree of accuracy. This is because transducers can be characterized by various shapes, sizes, frequencies, operation modes, and output intensities. Many utilize an array of independent elements that can operate in both continuous-wave and pulsed modes. Corresponding acoustic fields can possess complex three-dimensional structures: aside from targeted focal regions, transducers frequently create parasitic foci and grating lobes, either due to details of the source or inhomogeneities in tissue. Standard approaches for characterizing the field structure of ultrasound sources are based on point-by-point hydrophone measurements in water. However, direct hydrophone measurement of HIFU pressures is challenging for two reasons: (1) high pressure amplitudes require large measurement bandwidths and can damage hydrophones; and (2) large treatment volumes in conjunction with multiple operation modes (such as phased-array steering of the acoustic beam) require a prohibitive number of discrete measurements. Because of these challenges, as well as the complexity of holography and the difficulty in getting reliable results, acoustic holography has not been widely adopted in therapeutic ultrasound systems.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

The present technology is directed to array-based ultrasound systems configured to capture one or more characteristics of an acoustic beam, such as acoustic pressure, as the beam crosses a plane of the array. The array-based systems can capture the beam characteristic at a plurality of nodes arranged into a two-dimensional pattern, such as a rectangular grid. In some embodiments, the array-based ultrasound systems are configured to measure a two-dimensional distribution of a magnitude and a phase of the beam, such as a beam emitted from a focused or a non-focused ultrasound source. Array-based ultrasound systems of the present technology can include arrays having elongated elements with a first dimension that is about half of a wavelength of an emitted beam and a second dimension that is greater than a dimension of the emitted beam. The elongated elements can transmit signals corresponding to the beam characteristic such that the signals can be captured without a preamplifier and can be coupled to one or more multiplexers disposed within an array housing. Measurement of acoustic fields is an important aspect of ultrasound research and is required for regulatory purposes for new medical devices. These array-based systems and methods have a number of applications, such as diagnostic, therapeutic and cosmetic applications.

Certain details are set forth in the following description and FIGS. 1-9 to provide a thorough understanding of various embodiments of the disclosure. To avoid unnecessarily obscuring the description of the various embodiments of the disclosure, other details describing well-known structures and systems often associated with ultrasound technology, acoustic holography, piezoelectric arrays, and the components or devices associated with the manufacture of such structures are not set forth below. Moreover, many of the details and features shown in the Figures are merely illustrative of particular embodiments of the disclosure. Accordingly, other embodiments can have other details and features without departing from the spirit and scope of the present disclosure. A person of ordinary skill in the relevant art will therefore understand that the present technology, which includes associated devices, systems, and procedures, may include other embodiments with additional elements or steps, and/or may include other embodiments without several of the features or steps shown and described below with reference to FIGS. 1-9. Furthermore, various embodiments of the disclosure can include structures other than those illustrated in the Figures and are expressly not limited to the structures shown in the Figures.

I. ARRAY-BASED ULTRASOUND SYSTEMS AND ASSOCIATED STRUCTURES, DEVICES, AND METHODS

Figure 1:
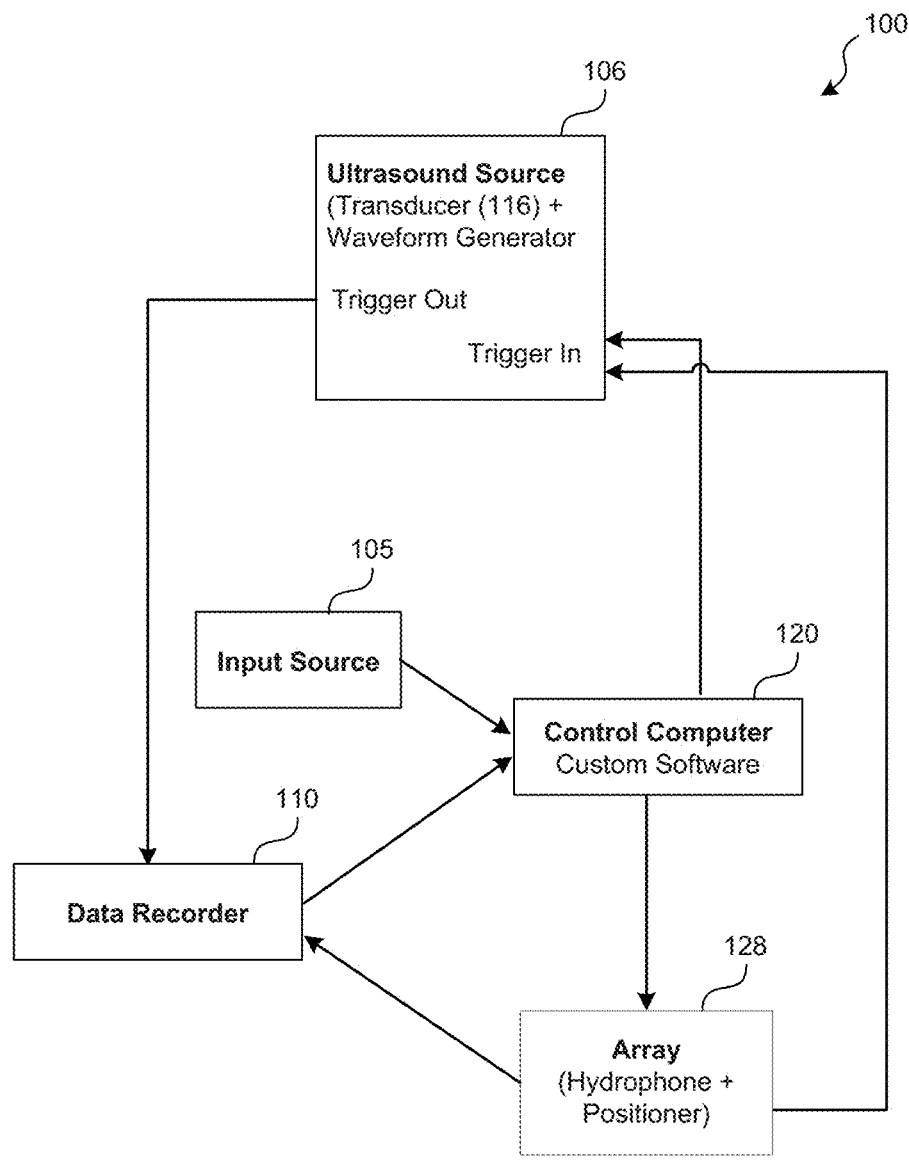
FIG. 1 is a schematic illustration of an array-based ultrasound system configured in accordance with embodiments of the technology.

FIG. 1 is a schematic illustration of an array-based ultrasound system ("system 100") configured in accordance with embodiments of the technology. The system 100 can be used to characterize and/or calibrate an ultrasound source, such as a diagnostic and/or therapeutic ultrasound source. The system 100 can be used to receive relevant user inputs, determine waveform measurement parameters, acquire these measurements, and perform subsequent analyses and calculations.

The system 100 can include an input device 105 capable of receiving inputs related to system components and/or operational characteristics. For example, in some embodiments, the input device 105 can receive inputs related to the geometry of an ultrasound transducer 116, the transducer's operational characteristics, and details of the hologram measurement apparatus. The transducer 116 geometry inputs can include the size and/or shape of a radiating surface on the transducer 116 and an approximate orientation of the transducer 116 in three-dimensional space. The operational characteristics shared with the input device 105 can include, for example, the frequency and Q-factor that describe the transducer's resonant characteristics, as well as the regime in which the transducer 116 is to be characterized, such as acoustic pressure of an emitted acoustic beam. The transducer's operational characteristics can further include a characterization as either continuous-wave (CW) or transient vibration, and output intensities that are consistent with either linear or nonlinear acoustic propagation between the transducer 116 and measurement sites. Inputs related to the measurement apparatus can include, for example, the size of an array 128, features of the array 128 such as a number of array elements (e.g., hydrophones), element sensing regions, bandwidth, and/or a reference position relative to a transducer 116. In some embodiments, details of the measurement apparatus can be defined by the user. The input device 105 can receive these inputs as user inputs, from a stored input source (e.g., a database), or directly from system components. In other embodiments, the input device 105 may include different features and/or have a different arrangement.

The input device 105 can pass the inputs to a control computer 120 capable of implementing an algorithm to identify waveform measurement parameters. The algorithm can utilize numerical and/or experimental studies of amplitude and phase distributions of acoustic fields radiated by representative clinical therapeutic ultrasound sources or other ultrasound sources. For example, the control computer 120 and algorithm may be configured to determine parameters such as the location and extent of a surface where measurements are to be acquired, the spacing between individual measurements on the surface, the temporal pulse time window relative to excitation of the transducer 116 during which each pressure measurement is captured, and/or a reverberation (blanking) period. Using these and/or other parameters, waveform measurements can be recorded and subsequent analysis and calculations can be performed. The control computer 120 can thus identify standard parameters for a given arrangement of a holography system.

The control computer 120 or other controller can instruct an ultrasound source 106 to generate and amplify a voltage waveform to excite a transducer 116. The ultrasound source 106 can be operably coupled to a function generator and, optionally, to an amplifier, such as a pre-amplifier. In some embodiments, the ultrasound source can have a frequency range of approximately about 0.5 to about 20 MHz. In other embodiments, however, the frequency of the ultrasound source can vary. The ultrasound source 106 can generate acoustic wave propagation, such as an emitted acoustic beam, between the transducer 116 and a measurement site having a hologram sensor (e.g., array 128). In some embodiments, the ultrasound source 106 includes a waveform generator 124. The transducer 116 can radiate sound while the waveform generator 124 generates and amplifies the voltage waveform used to excite the transducer 124. Data related to the acoustic wave propagation can be recorded by a data recorder 110. In further embodiments, the ultrasound source 106 can comprise another device having "trigger in" and "trigger out" capabilities that enable the transducer excitation to be synchronized with the position of the array 128 and the waveform acquisition by the data recorder 110.

As illustrated in FIG. 1, the array 128 can be a hologram sensor having a hydrophone or, is some embodiments, more than one hydrophone. In some variations, the array 128 can further include a positioner. Arrays configured in accordance with the present technology can be receiving arrays, such as one-dimensional receiving arrays, and can be configured as wide-aperture arrays. As will be described in greater detail with respect to FIG. 2, the array 128 can have a plurality of elongated elements disposed on an array surface, with individual elements sized and shaped to have a certain aspect ratio with a first dimension approximately half of a wavelength of an emitted beam and a second dimension that is greater than a diameter of the emitted beam. As such, the aspect ratios of each of the elongated elements are based upon the first dimension and the second dimension. Expected advantages of the first dimension include resolution of one or more characteristics (e.g., details) of the emitted beam. In some variations, the second dimension is a transverse extent of the emitted beam. Expected advantages of the second dimension include sizing and shaping the elongated elements to have a low electrical impedance so as to generate a signal that can be measured in the absence of preamplification or with minimal preamplification.

In some embodiments, the array 128 can be positioned about 50 mm, about 75 mm, about 100 mm, about 150 mm, or about 200 mm from the ultrasound source 106. In some embodiments, a center of the array 128 is positioned relative to the ultrasound source 106. For example, a focal line of the array 128 can be positioned on a plane of the ultrasound source 106. As described in greater detail with respect to FIG. 2, the array 128 can be configured to measure the acoustic waveforms on a measurement surface of the array 128 after the emitted beam crosses a plane of the array 128, such as a transverse plane of the array 128. The measurement surface of the array 128 can comprise, for example, a two-dimensional surface generally transverse to the wave propagation.

In operation, such as during a scan having an emitted acoustic beam, the array 128 can be advanced and/or rotated in increments. As discussed in greater detail with reference to FIGS. 6A and 6B, each increment can be sized to avoid aliasing. For example, each increment can be about half of a width of an acoustic beam wavelength or, alternatively, less than about half of the width of the acoustic beam wavelength. The array 128 can be advanced any number of increments such that a width of the acoustic beam is received by the array 128. For example, the array 128 can be advanced twice for each wavelength of the acoustic beam, or more than twice. In some embodiments, the array 128 can be advanced perpendicular to an axis of the acoustic beam. In further embodiments, the array 128 can be advanced in a pattern, such as a grid (e.g., a rectangular grid), having nodes with each increment represented by a node. Data related to one or more characteristics of the acoustic beam can be captured at each node.

The array 128 can further include one or more hydrophones and a positioner and can be configured to measure acoustic waveforms (e.g., pressure or velocity) of the emitted beam after crossing through a plane (e.g., a transverse plane) of the array 128. The array 128 can perform the measurements at points spanning a two-dimensional measurement region that may be generally oriented to be approximately perpendicular to the axis of the acoustic beam being measured.

A data recorder 110 can capture the acoustic waveforms measured by the array 128. The measurement parameters determined by an algorithm implemented by the custom software of the control computer 120 can be used to obtain, record, and analyze a hologram generated from the measured acoustic waveforms. For example, the scanning position, scanning extent, and step size determined by the algorithm can be used to configure the array 128. The duration of measurement acquisition determined by the algorithm can be used to configure the data recorder 110. And the duration and amplitude of excitation as determined by the algorithm can instruct the excitation of the ultrasound source 106.

Figure 5A:
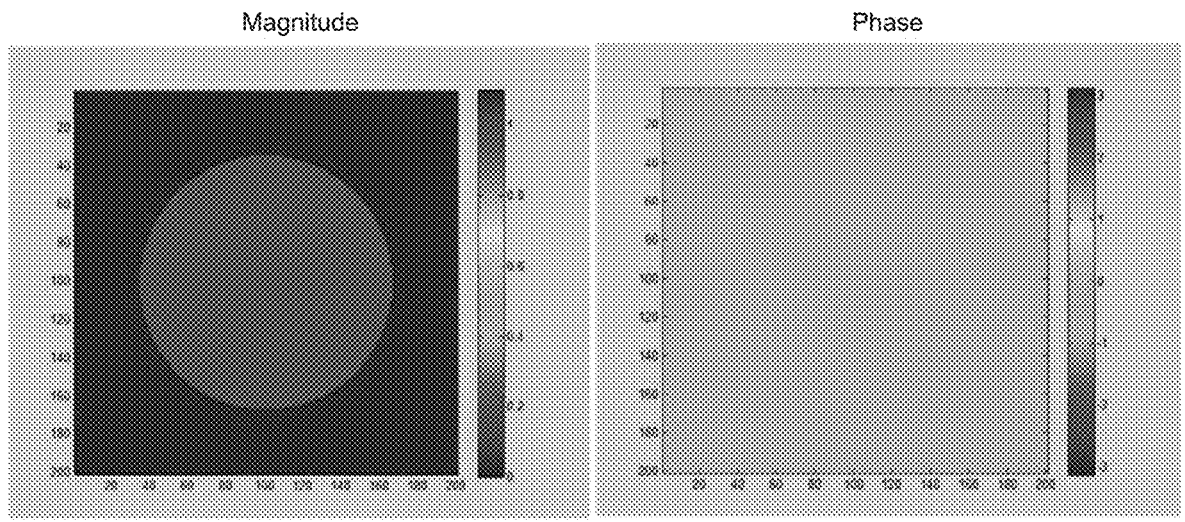
FIG. 5A is a graphical representation of an ideal hologram of a measured hologram of FIG. 5B for the array-based ultrasound system of FIG. 3A configured in accordance with embodiments of the technology.
Figure 5B:
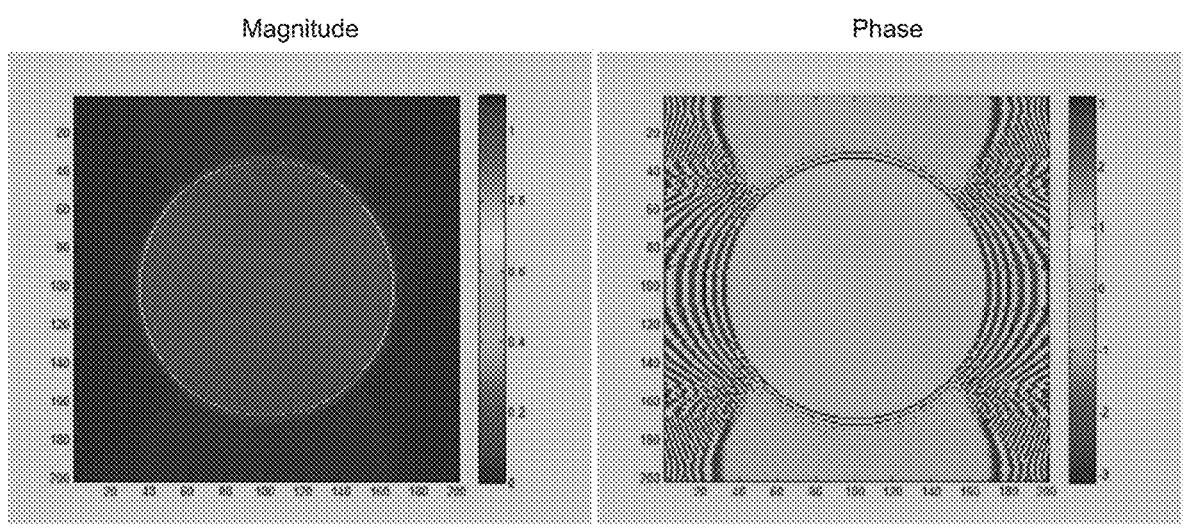
FIG. 5B is a graphical representation of the measured hologram for the array-based ultrasound system of FIG. 3A configured in accordance with embodiments of the technology.

A signal processor (not shown) can receive the acoustic waveform data from the data recorder 110 and can perform signal processing on the data in order to define and output a measured hologram from the raw measurements. Data related to a characteristic of the emitted acoustic beam, such as an acoustic waveform, can be processed to form a two-dimensional hologram representing the scan. The control computer 120 can, for example, process the data using an algorithm, such as a back-propagation algorithm, to mathematically reconstruct the scan into the two-dimensional hologram. In some embodiments, the characteristics of the acoustic beam can be acoustic pressure, velocity, or a combination thereof. In further embodiments, the scan can be mathematically reconstructed as a magnitude and/or phase distribution of the acoustic pressure or velocity in the transverse planes. An example of such reconstruction is shown in FIGS. 5A and 5B.

As will be discussed in further detail below with reference to FIGS. 4B-5B, backward projections can determine the vibrations on the surface of the array 128. In some embodiments, the system 100 can auto-focus the source hologram (e.g., angle and distance) for alignment based on the measured hologram. As will be discussed in further detail below with reference to FIG. 9, the measured holograms can be used to calibrate and/or re-calibrate the ultrasound source 106. In some embodiments, a series of holograms recorded over a range of output levels can be used to fully characterize source output levels. In further embodiments, additional or alternate characteristics can be calculated.

The approximate position of the array 128 relative to the transducer 116 need not be known with a high degree of accuracy because the measured hologram captures the full three-dimensional acoustic field, and the position of the transducer 116 can be inferred from backward projection calculations. Explicit requirements regarding the positional accuracy with which the array 128 is interfaced to the transducer 116 may be warranted to meet strict measurement standards. However, in many cases it can be sufficient to orient the array 128 to be perpendicular to the acoustic axis of the transducer 116 ("by eye"); then the distance between array 128 and the transducer 116 can be estimated by identifying the position of the acoustic focus or by measuring time of flight.

Based on the measured hologram, the system 100 can utilize a control computer (i.e., the control computer 120 or another control computer) to generate a measured hologram corresponding to one or more characteristics of the ultrasound source 106. For example, the characteristics can include forward and backward projections (using linear or nonlinear acoustic propagation), radiation force calculations for specified targets, and calculations of the true acoustic power. In some embodiments, system 100 can include a multiplexer, a preamplifier, or a combination thereof. In other embodiments, system 100 can include a multiplexer and can be configured to operate in the absence of a preamplifier.

The control computer 120 can instruct the various components in the manner described above to generate acoustic waves, sense, receive, record, measure, and/or analyze a measured hologram, and make calculations based on this measured hologram. For example, based on the measured hologram, the system 100 can utilize the control computer 120 to generate one or more of the characteristics of the ultrasound source 106 described above: forward and backward projections, radiation force calculations for specified targets, and calculations of the true acoustic power. In additional embodiments, the system 100 can utilize the control computer 120 to determine one or more holography measurement parameters, instruct the hologram sensor to measure one or more characteristics of the acoustic beam after the beam crosses the array surface, and in some instances, generate one or more reconstructions of the beam characteristic. In further embodiments, additional or alternate characteristics can be calculated by the control computer 120.

The control computer 120, processor, or other computing devices on which the system 100 is implemented may include a central processing unit, memory, input devices (e.g., keyboard and pointing devices), output devices (e.g., display devices), and storage devices (e.g., disk drives). The memory and storage devices are computer-readable media that may be encoded with computer-executable instructions that implement the object permission enforcement system, which means a computer-readable medium that contains the instructions. In addition, the instructions, data structures, and message structures may be stored or transmitted via a data transmission medium, such as a signal on a communications link and may be encrypted. Various communications links may be used, such as the Internet, a local area network, a wide area network, a point-to-point dial-up connection, a cell phone network, and so on.

The acoustic holography system may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

Embodiments of the acoustic holography system may be implemented in and used with various operating environments that include personal computers, server computers, handheld or laptop devices, multiprocessor systems, microprocessor-based systems, programmable consumer electronics, digital cameras, network PCs, minicomputers, mainframe computers, computing environments that include any of the above systems or devices, and so on.

Figure 2:
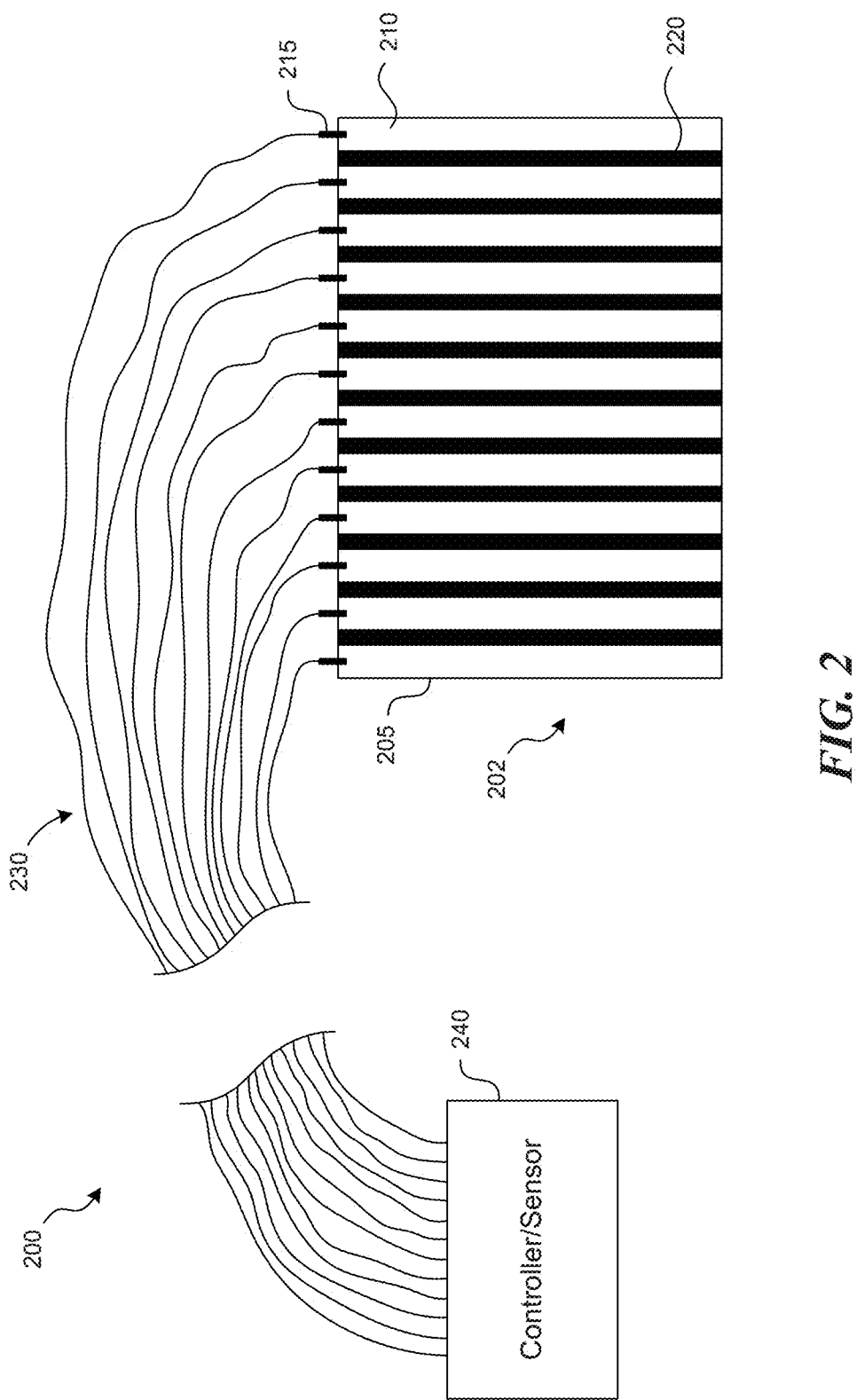
FIG. 2 is a partially schematic illustration of an array configured in accordance with the present technology.

FIG. 2 is a partially schematic illustration of an array system ("array system 200") configured in accordance with the present technology. The array system 200, and other array systems configured in accordance with the present technology, can be used to standardize the implementation of acoustic holography for diagnostic and/or therapeutic ultrasound sources. The array system 200 can be used to measure one or more characteristics of an acoustic beam emitted from an ultrasound source. An array 202 of the array system 200, and other arrays configured in accordance with the present technology, can be receiving arrays configured as one-dimensional linear arrays. Unlike conventional arrays, array 202 and arrays configured in accordance with the present technology can be wide-aperture arrays and can include elements that each have a greater area and strong signals compared to conventional array elements. In some embodiments, the array 202, and arrays configured in accordance with the present technology, can be configured for multiplexing based on the plurality of elements acquiring data.

As illustrated in FIG. 2, array 202 can include a plurality of elongated elements 210 disposed on the surface 205 of the array 202. The elongated elements 210 can have an aspect ratio where at least one dimension of the elongated element 210 is greater than a width of the acoustic beam emitted at a certain frequency. In some embodiments, a height or a length of the elongated elements 210 is larger than the width of the acoustic beam emitted at a certain frequency and a width of the elongated elements 210 is about half of a wavelength of the acoustic beam emitted at the certain frequency.

The array 202 can include any number of elongated elements 210 suitable for receiving at least one characteristic about the acoustic beam. In some embodiments, the number of elongated elements 210 can be selected based on the frequency of the acoustic beam. In some embodiments, for example, the array 202 can have about 10 elements, about 20, about 30, about 40, about 50, about 100, about 150, about 200, about 300 elements, about 500 elements, about 750 elements, or about 1000 elements.

The elongated elements 210 can be spaced apart along the surface 205 at a distance measured from a center line of a first elongated element to a center line of a second elongated element. The distance between the first and second center lines can be selected such that one or more corresponding side-lobes of a directivity pattern are directed aside from the ultrasound source, such as about 0.75 mm. In other embodiments, the distance between the first and the second center lines can be about 0.25 mm, about 0.50 mm, or about 100 mm, about 125 mm, about 150 mm, about 175 mm, or about 200 mm. For example, in particular embodiments the distance between the first and second center lines is about 0.75 mm for wavelengths of about 1 MHz, about 0.25 mm for wavelengths of about 3 MHz, and about 100 mm for wavelengths of about 7.5 kHz. In some embodiments, directing the corresponding side-lobes aside from the ultrasound source can avoid aliasing effects. In these embodiments, a corresponding distance is less than about half of the width of the acoustic beam wavelength. Either a shape of the elongated elements 210 or a displacement method can achieve sufficient resolution of at least one characteristic of the acoustic beam in a longitudinal direction along the elongated element 210, such as a longitudinal direction perpendicular to a center line of the array 202.

The elongated elements 210 can be configured to receive at least one characteristic of an acoustic beam having any shape or any size. In some embodiments, for example, the array 202 can be configured to receive at least one characteristic of the acoustic beam having a frequency of about 0.5 to about 3 megahertz (MHz), such as about 1 MHz or about 2 MHz. The elongated elements 210 can be sized and shaped to have a desired aspect ratio based on the frequency of the acoustic beam. In some embodiments, each elongated element has a first dimension and a second dimension. For example, the first dimension of each elongated element 210 can be larger than a width of an acoustic beam, such as about 50 mm to about 100 mm and the second dimension can be smaller than half of a wavelength of an ultrasound beam, such as about 0.75 mm when the beam wavelength is about 1 MHz. In other embodiments, the second dimension is about about 1, about 1.1, about 1.2, about 1.3, about 1.4, or about 1.5 times larger than the width of the acoustic beam. In some variations, the array 202 can be configured with about 100 to about 200 elements 210 each having a first dimension of about 50 to about 100 mm and the second dimension of about 0.75 mm. In other embodiments, however, elongated elements 210 of the array 202 may have different dimensions and/or the array 202 may have a different arrangement of elongated elements 210.

In some embodiments, the array 202 can have surface 205 with a height and a width that exceeds a dimension of the acoustic beam, such as a height of about 190 mm and a width of about 140 mm. In other embodiments, the surface 205 of the array 202 can have a height of about 50 mm, about 100 mm, about 110 mm, about 120 mm, about 130 mm, about 140 mm, about 150 mm, about 160 mm, about 170 mm, about 180 mm, about 190 mm, about 200 mm, about 300 mm, about 400 mm, or about 500 mm, and a width of about 50 mm, about 100 mm, about 110 mm, about 120 mm, about 130 mm, about 140 mm, about 150 mm, about 160 mm, about 170 mm, about 180 mm, about 190 mm, about 200 mm, about 300 mm, about 400 mm, or about 500 mm.

As illustrated, the surface 205 can be flat. In other embodiments (such as the arrangement discussed below with reference to FIGS. 3A and 3B), the surface 205 can have other shapes and configurations. Similarly, the elongated elements 210 disposed on the surface 205 can be flat or can have other shapes and configurations depending on the shape of the surface 205. The array 202 can further comprise a housing (not shown) extending beyond the surface 205. In some embodiments, the housing can be configured to minimize an interaction of one or more edge waves from interfering with the elements 210 receiving at least one or more characteristics of the acoustic beam, such as an incident pressure field.

In some embodiments, the elongated elements 210 can form a pattern on the surface 205 of the array 202. As illustrated in FIG. 2, the elements 210 of the array 202 are disposed in a linear pattern on the surface 205 of the array. In other embodiments, however, elongated elements can have a variety of shapes and can be disposed on an array surface in a variety of different patterns.

Figure 3A:
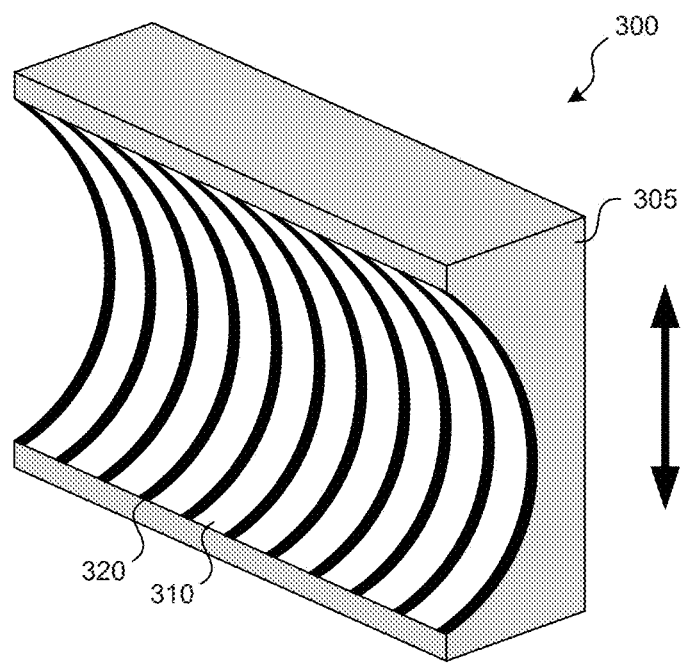
FIG. 3A is a partially schematic illustration of an array configured in accordance with embodiments of the technology.
Figure 3B:
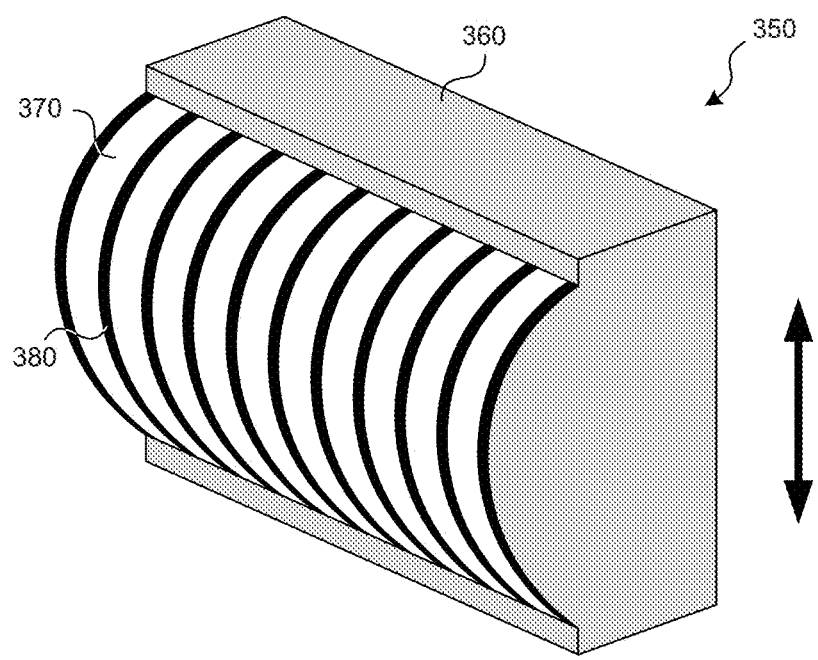
FIG. 3B is a partially schematic illustration of an array configured in accordance with embodiments of the technology.

The array 202 can have at least a partially metallized surface and can be fabricated from a piezoelectric material. Suitable piezoelectric materials can include, for example, a piezoelectric polymer including polyvinylidene fluoride (PVDF), piezopaint, another ink-jet delivered piezo materials, or a piezoelectric material with low acoustic impedance, such as an acoustic impedance similar to water. The piezoelectric material can be stretched over the surface 205, which can be a lens disposed upon a substrate 220. With reference to FIGS. 3A and 3B, the lens can be a cylindrical lens, such as a concave or convex lens. In some embodiments, the substrate 220 can be a backing material. The substrate 220 can have an attenuation configured to reduce acoustic cross-talk between elongated elements 210 of the array 202. In some embodiments, the substrate 220 is a metal or ceramic powder-loaded epoxy material or a rubber material. The piezoelectric membrane can be adhered to the backing material by a curing process. For example, the array may be spot-poled or field-poled across the entire membrane.

In some embodiments, the elongated elements 210 can have a metallized surface and can be formed from of a metallized material by any suitable process. For example, the elongated elements 210 can be formed by etching the metallized surface to remove at least some of an electrically conductive surface of the metallized material and retaining at least some of the piezoelectric material. The elongated elements 210 can be electrically isolated, for example by portions of the substrate 220, such that a charge of the acoustic wave is independently measured across each elongated element 210 of the array. The substrate 220 can be formed of any suitable material having an impedance similar to water with a high absorption, such as a stabilizing material.

As illustrated in FIG. 2, the array system 200 can include an array 202 and a receiver 240 (e.g., a data acquisition unit), such as a multichannel electronic receiver (e.g., a Verasonics® engine or similar). The array 202 can be coupled to the receiver 240 by a plurality of circuits, with each circuit formed between one of the elements 210 and a channel of the receiver 240 by a cable 230 and a connector 215. In some embodiments, the elements 210 can be connected to the receiver 240 using a flex-circuit, a multiplexer, or a combination thereof, to reduce a number of cables 230 connecting the array 202 to the receiver 240.

Arrays configured in accordance with the present technology, such as array 202, can measure at least one characteristic of an acoustic beam without being coupled to a preamplifier. For example, array 202 having elements 210 with an aspect ratio of at least one dimension of the elongated element 210 is greater than a width of the acoustic beam can be used in the absence of a preamplifier. In these embodiments, arrays configured in accordance with the present technology can be coupled to one or more multiplexers. The arrays can be configured to carry one or more multiplexers in a housing of the array. When configured to carry a multiplexer in the housing, the arrays can have fewer output wires compared to arrays that are coupled to an external multiplexer.

FIG. 3A is a partially schematic illustration of an array ("array 300") configured in accordance with embodiments of the present technology. The array 300 can have cylindrically shaped elongated elements 310 formed over stabilizing material 320 within housing 305 using the methods described with reference to FIG. 2. As illustrated, the array 300 is a one-dimensional array having a convex array surface and convex elongated elements 310 disposed thereon. The array 300 can have a curvature radius of about 100 mm and an angular aperture of about 90°. In other embodiments, the curvature radius can be about 30 to about 100 mm and an angular aperture of about about 60 degrees to about 100 degrees which can be a full aperture angle.

FIG. 3B is a partially schematic illustration of an array ("array 350") configured in accordance with additional embodiments of the present technology. The array 350 can have cylindrically shaped elongated elements 370 formed over stabilizing material 380 within housing 360 using the methods described with reference to FIG. 2. As illustrated, for example, the array 350 is a one-dimensional array having a concave array surface and concave elongated elements 370 disposed thereon.

Figure 4A:
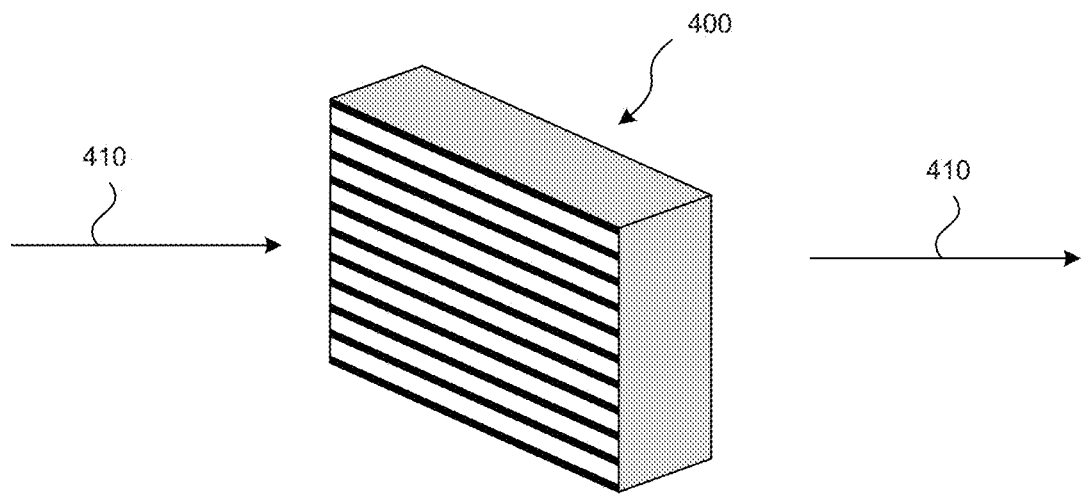
FIG. 4A is a side-view of a detection configuration for an array configured in accordance with embodiments of the technology.
Figure 4B:
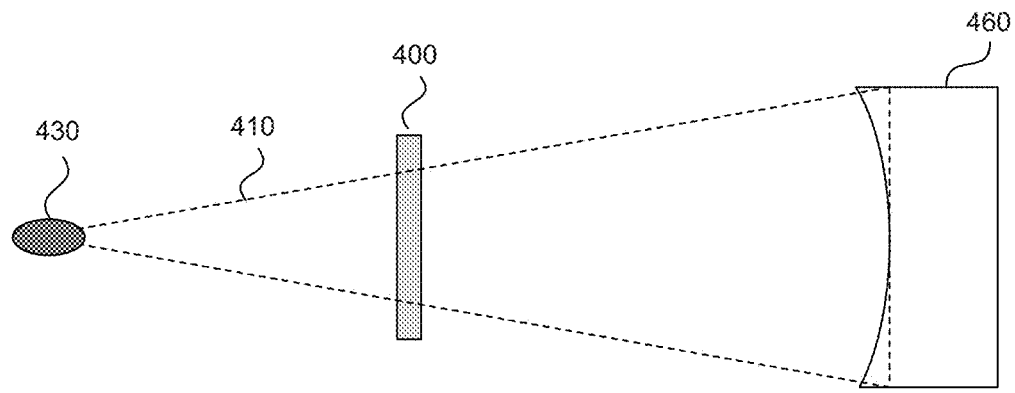
FIG. 4B is a side-view of a measurement configuration for an array configured in accordance with embodiments of the technology.

FIG. 4A is a side view of a detection configuration for an array ("array 400") configured in accordance with further embodiments of the present technology. FIG. 4B is a side-view of a measurement configuration for array 400 configured in accordance with embodiments of the technology. Referring to FIGS. 4A and 4B together, an acoustic beam 410 can be emitted towards a transverse plane of the array 400. The array 400 can be positioned between an ultrasound source 460 and a focal point 430 (e.g., a measurement surface) such that the acoustic wave propagates in one direction through a transverse plane of the array 400 towards the focal point 430. The arrangement illustrated in FIG. 4B can be used to obtain a source hologram in the manner described below with reference to FIGS. 5A, 5B, and 7. For example, the system 100 discussed above with reference to FIG. 1 can be used to obtain a measured hologram on a scan plane measurement surface 460. The measurement surface 460 can comprise a two-dimensional surface generally transverse to the acoustic beam 410.

In various embodiments, scan points can be selected from coordinates within a rectangular grid or non-rectangular pattern on a plane, such as a two-dimensional grid. As described above with reference to FIG. 1, the array 400 can be incrementally moved in a pattern, such as a pattern defined by the rectangular grid, to scan one of the two dimensions of coordinates in a transverse position or at an angle. The measured hologram on the measurement surface 460 can be used in calculations to determine the source hologram representing vibrations on the surface of the array 400. In some embodiments, the system can auto-focus the source hologram (e.g., angle and distance) for alignment. The source hologram may be useful in itself to provide a record of source performance for quality assurance purposes. In addition, source holograms and measured holograms may be used to define boundary conditions for linear or nonlinear acoustic propagation calculations. Propagation calculations can determine vibrations at the transducer surface as a source hologram, or in a three-dimensional pressure field in an acoustic medium with known properties, such as water or tissue.

FIG. 5A is a graphical representation of an ideal hologram of a measured hologram of FIG. 5B for the array-based ultrasound system of FIG. 3A configured in accordance with embodiments of the technology. FIG. 5B is a graphical representation of the measured hologram for the array-based ultrasound system of FIG. 3A configured in accordance with embodiments of the technology.

Referring to both FIGS. 5A and 5B, the holograms include magnitude and phase measurements. Both magnitude and phase components of the source hologram (shown in FIG. 5B) illustrate the expected pattern of array elements corresponding to array 300 illustrated in FIG. 3A. FIG. 5B represents a hologram reconstructed at a surface corresponding to a physical surface of an ultrasound source. The reconstruction illustrated in FIG. 5B is based on a measured hologram recorded over a different surface. For example, the reconstructed hologram of FIG. 5B is a reconstruction of a normal velocity magnitude and phase on a surface of a 100 mm diameter 1 MHz circular piston ultrasound source by a convex cylindrically shaped array such as array 300 of FIG. 3A. The representation illustrated in FIG. 5B could be reconstructed from an array having 256 elements spaced apart by 0.75 mm measured from center lines of the elements positioned on an array surface of about 192 mm wide by about 141 mm long. In some embodiments, the representation of FIG. 5B can be reconstructed from an array having a curved surface, such as a curvature radius of about 100 mm and an angular aperture of 90°, when a center of the array is positioned about 100 mm from an ultrasound source.

For this reconstruction, a focal line of the array can be positioned on a plane of the ultrasound source.

Aside from acoustic propagation, other types of calculations based on predicted holograms, measured holograms, and reconstructed holograms can be directly relevant to therapeutic and/or diagnostic sources. For example, the measured hologram can be used to calculate the true acoustic output power of the source as the emitted acoustic beam crosses the transverse plane of the array and calculate the radiation forces that would occur if the acoustic beam impinged on particular targets. Acoustic output power can be estimated from a spatial distribution of pressure magnitude measurements, phase magnitude measurements, or a combination thereof. However, such an approach typically assumes that the acoustic beam comprises a plane wave and is not correct for an arbitrary acoustic beam (such as that generated by a focused source). Because a measured hologram incorporates phase information, it can be used to calculate the true power of an arbitrary beam, and this calculation can be performed efficiently using an angular spectrum approach.

In addition, measured holograms can be used to calculate radiation forces on target objects, which may be useful in itself (e.g., for pushing kidney stones). Further, because a hologram permits calculation of the radiation force on a perfectly absorbing target, a hydrophone's sensitivity at a single frequency can be calibrated by comparing a measured hologram to analogous measurements made with a radiation force balance. Because the uncertainty associated with radiation force balance measurements can be significantly less than that associated with laser vibrometry at megahertz frequencies, single-frequency hydrophone calibrations using an approach based on holography may be comparable to or better than primary calibrations that rely on laser vibrometry.

Figure 6A:
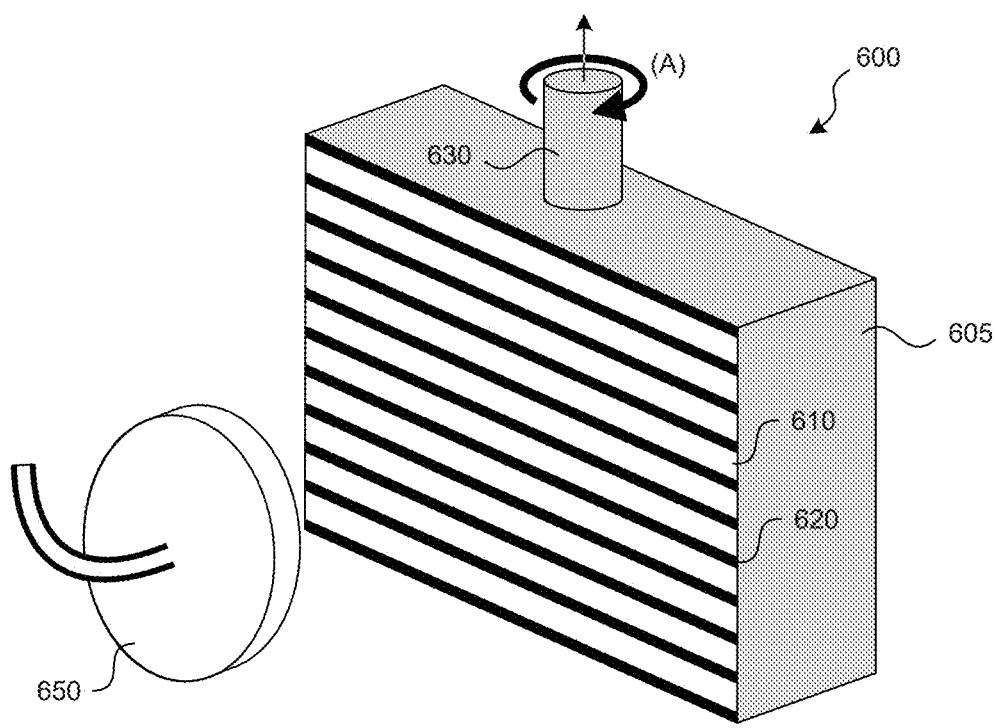
FIG. 6A is a partially schematic illustration of an array configured in accordance with embodiments of the technology.
Figure 6B:
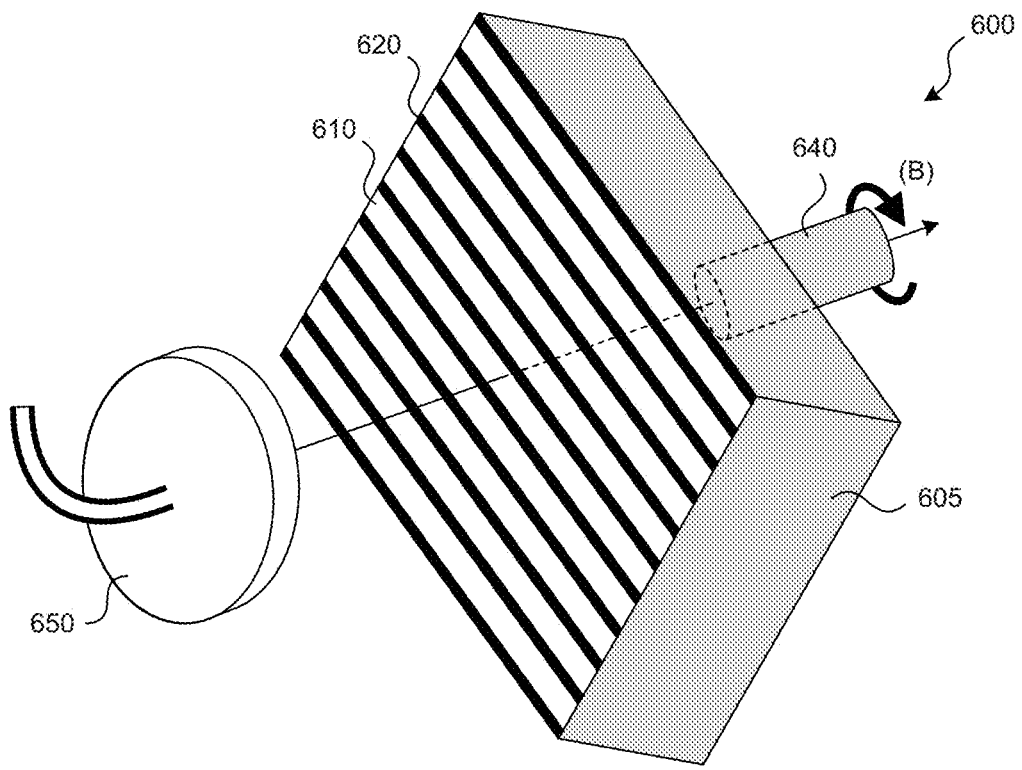
FIG. 6B is a partially schematic illustration of an array configured in accordance with embodiments of the technology.

FIG. 6A is a partially schematic illustration of an array ("array 600") configured in accordance with embodiments of the present technology. FIG. 6B is a partially schematic illustration of the array 600 configured in accordance with other embodiments of the technology. Referring to FIGS. 6A and 6B together, the array 600 can have features generally similar to those of the arrays illustrated in FIGS. 2-4B. For example, the array 600 can have elongated elements 610 disposed on a surface electrically isolated by a substrate 620 and a housing 605. In other embodiments, the array 600 can have a single element, such as a single ribbon element. As illustrated, the array 600 can initially be positioned at a location that, when a beam is emitted from an ultrasound source 650, the emitted beam crosses at least one plane of the array 600. After crossing the plane of the array, data from the emitted beam can be captured by a camera (not shown).

The array 600 can be coupled to a positioner (not shown), such as an angular positioner, that can be controlled by a computer to rotate the array 600. In some embodiments, the array 600 can be rotated around one or more axes 630 and 640, such as a first axis 630 that is parallel to a surface of the array 600 and perpendicular to the elements 610 disposed thereon, a second axis 640 that is perpendicular to a surface of the array 600, or a combination thereof. In other embodiments, the ultrasound source 650 can be rotated about the first axis 630, the second axis 640, or both axes while the array 600 is held in a generally stationary position.

In other embodiments, the array 600 can be rotated in increments. Similar to arrays 128, 200, 300, and 400, each increment of the rotation can be sized to avoid aliasing. For example, each increment can be about half of a width of an acoustic beam wavelength or less than about half of the width of the acoustic beam wavelength. The array 600 can be rotated by any number of increments, including the increments described above with respect to FIG. 1, such that a width of the acoustic beam is received by the array 600. In some embodiments, the array 600 can be rotated in a pattern having nodes that represent each increment. In further embodiments, the array 600 can be moved to various positions within an acoustic field of the acoustic beam, such as a large or unfocused acoustic beam. For example, the array 600 can be translated to one or more locations and can be configured to receive, detect, and/or record data corresponding to at least one characteristic of the acoustic field at each location. By rotation the array 600, data points can be recorded at a plurality of angular planes of the acoustic beam.

In operation and regardless of whether the array 600 or the ultrasound source 650 is rotated, the array 600 can be rotated to acquire data from the acoustic beam at about 50 angles, about 100 angles, about 150 angles, or about 200 angles and can acquire data from about 50 hits, about 100 hits, about 150 hits, or about 200 hits of the acoustic beam crossing the transverse plane of the array 600. For example, during a data acquisition from the emitted acoustic beam, the array 600 can be rotated around the first axis 630 and the second axis 640 such that the array 600 is positioned to acquire about 100 hits at about 100 different angles to yield about 10,000 data points.

The data acquired from each of the locations can be reconstructed from a composite hologram, for example, using the control computer 120 of FIG. 1. In some embodiments, data reconstruction can include calculations of one or more characteristics of the acoustic beam can be based on signals received and/or detected by the elements 610. For example, the signals can be used to calculate one or more two-dimensional angular spectrum components of the acoustic beam.

Further details regarding ultrasound system components and operating parameters can be found in U.S. patent application Ser. No. 13/085,368, filed Apr. 12, 2011 and entitled "Methods and Systems for Non-Invasive Treatment of Tissue Using High Intensity Focused Ultrasound Therapy" and U.S. patent application Ser. No. 13/894,333 filed May 14, 2013 and entitled "Portable Acoustic Holography Systems for Therapeutic Ultrasound sources and Associated Devices and Methods," both of which are hereby incorporated by reference in their entireties.

II. METHODS OF USING ARRAY-BASED ULTRASOUND SYSTEMS AND OTHER STRUCTURES AND ASSOCIATED SYSTEMS

Figure 7:
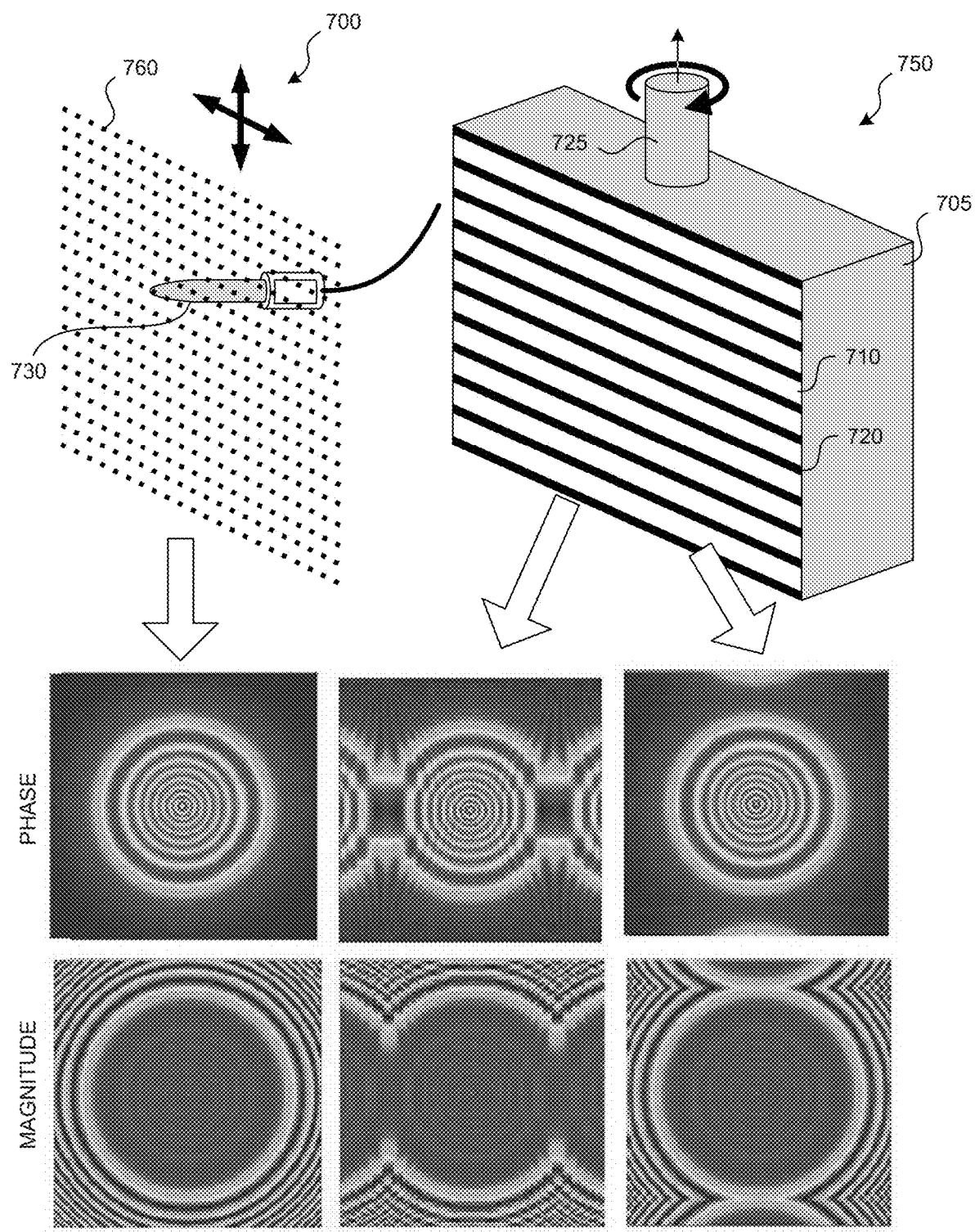
FIG. 7 is a partially schematic illustration of elements of an array-based ultrasound system having the array of FIG. 6A and graphical representations of holograms configured in accordance with embodiments of the technology.

FIG. 7 includes a partially schematic illustration of array 750, a hydrophone raster scanning system ("raster system 700") and graphical representations of holograms configured in accordance with an embodiment of the disclosed technology. In the example illustrated in FIG. 7, the raster system 700 and array 750 holograms are reconstruction models of lateral pressure distribution of an ultrasound source beam (e.g., a piston source beam) emitted at about 1 MHz, such as pressure magnitude and phase based on the angular field scan. Distortions in the holograms reflect artifacts of the angular field scan, for example, artifacts from an insufficient (e.g., too small) angular step (middle column) or from an insufficient height of the array 750 (right column). The example illustrated in FIG. 7 is one particular example associated with embodiments of the present technology.

The holograms correspond to reconstructions of the raster system 700 (left column), the array 750 (middle column), and another array (right column, and array not shown). The top row of holograms represents phase reconstructions and the bottom row represents magnitude reconstructions. The raster system 700 holograms (left column) illustrate Rayleigh-integral simulations of a measurement by a raster-scanned point receiver performed by a hydrophone 730 according to a two-dimensional raster array 760. The simulations were performed using the following parameters, the single hydrophone 730 is positioned about 100 mm from the raster scan 760 which includes elongated elements having a distance of about 0.75 mm between center lines of the elongated elements corresponding to half of a wavelength width of an emitted beam. The raster system 700 further includes a scan point receiver (not shown). The illustrated array 750 is about 192 mm long and about 150 mm wide and configured as a one-dimensional array.

The array holograms illustrate graphical representations of a reconstruction model depicting data obtained from an angular field scan (middle and right columns). Referring to the holograms in the middle column, the reconstructions model an angular field scan and an array having the following characteristics: during the angular field scan, the array 750 is rotated about) 90° (±45°) for about 100 angular increments where the rotation of each increment is about 0.9°. The array 750 includes 256 elongated elements 710 (all 256 elongated elements are not shown) having a distance of about 0.75 mm between center lines of the elongated elements 710 corresponding to half of a wavelength width of an emitted beam. The array 750 can be about 192 mm long and about 150 mm wide and can be positioned about 100 mm from an ultrasound source (not shown). Referring to the holograms in the right column, the reconstructions model an angular field scan and an array having the following characteristics; during the angular field scan, the array (not shown) is rotated about 90° (±45°) for about 200 angular increments where the rotation of each increment is about 0.45°. The array can include 160 elongated elements having a distance of about 0.75 mm between center lines of the elongated elements corresponding to half of a wavelength width of an emitted beam. The array can be about 120 mm long and about 150 mm wide and can be positioned about 100 mm from an ultrasound source (not shown).

Figure 8:
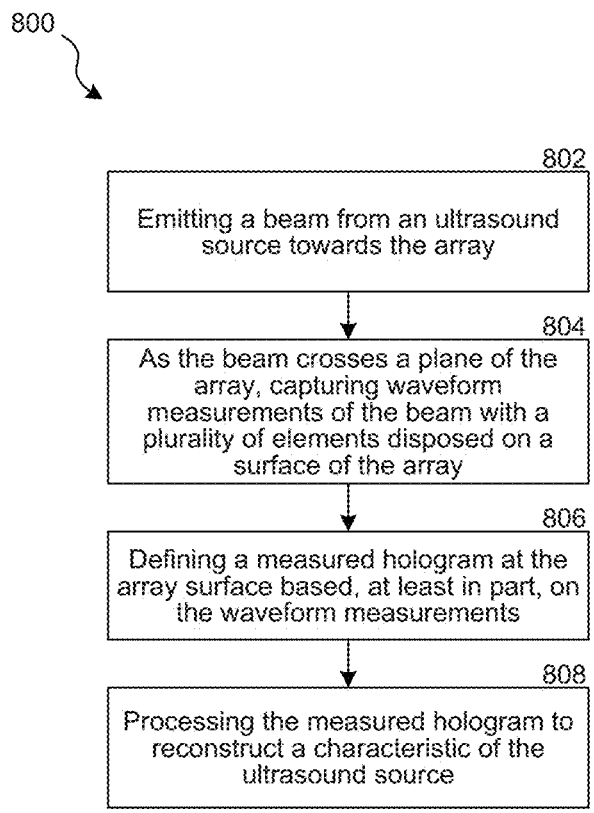
FIG. 8 is a block diagram illustrating a method of characterizing an ultrasound source using an array-based ultrasound system in accordance with embodiments of the present technology.

FIG. 8 is a block diagram illustrating a method 800 of measuring at least one characteristic of an ultrasound source using an array-based acoustic holography system in accordance with embodiments of the technology. At block 802, the method 800 can include emitting a beam from an ultrasound source towards an array. In some embodiments, emitting a beam includes emitting the beam having a beam characteristic based, at least in part, on one or more holography measurement parameters. In further embodiments, one or more holography measurement parameters are a size of a hydrophone sensing region, a hydrophone bandwidth, or a reference position relative to a transducer at which the hydrophone is initially located. The ultrasound source can have an amplitude of excitation from about 1 megahertz to about 2 megahertz.

In some embodiments, prior to emitting the beam from the ultrasound source at bock 802, the method can include obtaining a transducer geometry characteristic, a transducer operation characteristic, and a holography system measurement characteristic. In some embodiments, obtaining a transducer geometry characteristic includes obtaining at least one of an aperture size, planar or curvature characteristic, orientation, or shape of a radiating transducer. Obtaining a transducer operation characteristic can include obtaining at least one of a linear, nonlinear, pulsing, continuous, spatial extent, Q-factor, or operating frequency characteristic of a radiating transducer. In some embodiments, obtaining a holography system measurement characteristic includes obtaining at least one of a size of a hydrophone sensing region, a hydrophone bandwidth, a geometry of a test tank, a liquid temperature in the test tank, or a reference position relative to a transducer at which the hydrophone is initially located.

As the beam crosses a transverse plane of the array, at block 804 the method 800 includes capturing waveform measurements of the beam with a plurality of elongated elements disposed on a surface of the array. In some embodiments, capturing waveform measurements of the beam with the plurality of elongated elements includes capturing waveform measurements of the beam crossing the transverse plane of the array and scanning two or more elongated elements of the plurality. At least one element of the plurality can have a convex shape, a concave shape, or a flat shape, and each element of the plurality can have an aspect ratio larger than a width of the acoustic beam.

In further embodiments, capturing waveform measurements of the beam with the plurality of elongated elements includes moving the ultrasound source relative to the array, moving the array relative to the ultrasound source, or moving both the ultrasound source and the array. Moving the array or moving both the ultrasound source and the array can include moving the array or moving both the ultrasound source and the array stepwise, linearly, or angularly. In some embodiments, the stepwise movement includes one or more steps. Each step can be less than half of a wavelength of the acoustic beam. The linear can include movement in a first direction perpendicular to a height of the array, and the angular movement includes movement in a second direction angularly around a first axis or a second axis, the first axis parallel to the array surface and perpendicular to at least one element and the second axis perpendicular to the array surface.

At block 806, the method 800 includes defining a measured hologram at the array surface based, at least in part, on the waveform measurements. At block 808, the method 800 includes processing the measured hologram to reconstruct a characteristic of the ultrasound source. In some embodiments, processing the measured hologram to reconstruct at least one characteristic of the ultrasound source includes reconstructing one or more two-dimensional acoustic field characteristics of the ultrasound source. The two-dimensional acoustic field characteristics can include acoustic pressure magnitude and phase. In further embodiments, processing the measured hologram to reconstruct the characteristic of the ultrasound source includes using the hologram to define a boundary condition of the ultrasound source. In some embodiments, processing the measured hologram to reconstruct the characteristic of the ultrasound source includes determining at least one of an acoustic output power of the ultrasound source or a radiation force that would occur if an acoustic beam from the ultrasound source impinged on a particular physical target.

In further embodiments, processing the measured hologram further includes instructing a control computer to determine holography measurement parameters. In some embodiments, the measurement parameters can include at least one of a scanning position, a scanning extent, or step size of a hologram sensor, a duration of measurement acquisition of a data recorder, or a duration or amplitude of excitation of the ultrasound source. In further embodiments, based on the holography measurement parameters, the method 800 can include scanning a target surface to capture waveform measurements at a plurality of points on the target surface. In some embodiments, a two-dimensional target surface is scanned. The scanning can be continuous, pulsed, or otherwise intermittent. At block 808, the method 800 includes using the waveform measurements to define a measured hologram of the acoustic field on the target surface.

In other embodiments, holograms are used to define boundary conditions for calculating two-dimensional and/or three-dimensional acoustic field characteristics of the ultrasound source. In particular embodiments, such calculations are performed by applying at least one of a Rayleigh integral, Helmholtz-Kirchhoff integral, Khokhlov-Zabolotskaya-Kuznetsov ("KZK") equation, or a Westervelt equation. These calculations can determine pressure waveforms (including shock waves), estimate heating rates, and/or account for tissue attenuation by scaling the source amplitude. The method 800 can be performed for linear or nonlinear acoustics, and for uniform or nonuniform media.

In some embodiments, processing the measured hologram to reconstruct a characteristic of the ultrasound source includes determining at least one of an acoustic output power of the ultrasound source or a radiation force that would occur if an acoustic beam from the ultrasound source impinged on a particular target. In a particular embodiment, for example, the radiation force can be used in conjunction with an independent radiation force balance measurement to calibrate a hydrophone's sensitivity at a single frequency.

Figure 9:
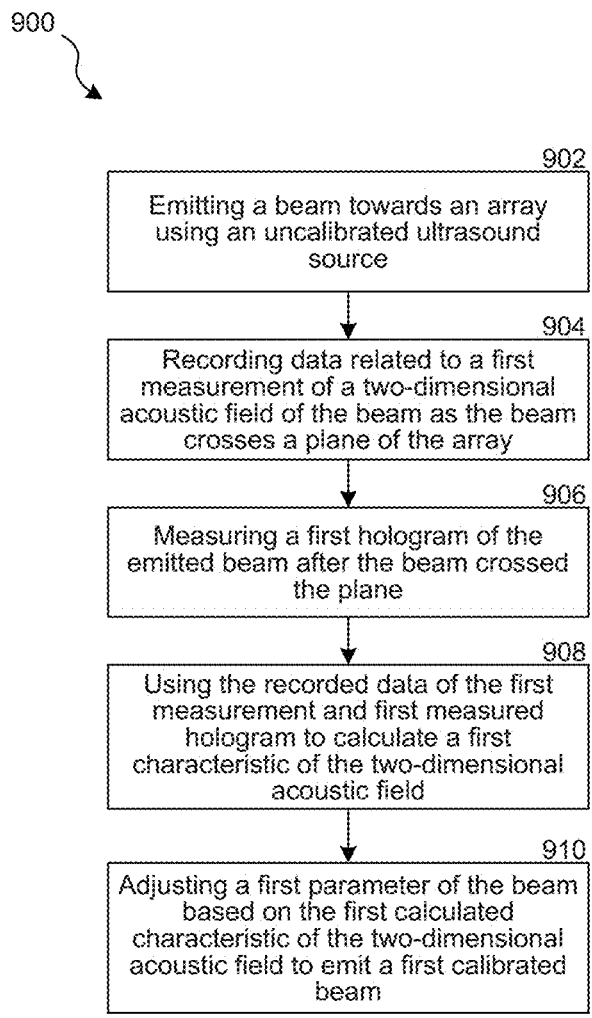
FIG. 9 is a block diagram illustrating a method of calibrating an ultrasound source using an array-based ultrasound system in accordance with embodiments of the present technology.

FIG. 9 is a block diagram illustrating a method 900 of calibrating an ultrasound source in accordance with embodiments of the technology. In several embodiments, for example, the hydrophone sensitivity can be calibrated at a single frequency. At block 902, the method 900 can include emitting a beam towards an array using an uncalibrated ultrasound source. In some embodiments, the hologram is measured using the method 800 described above with reference to FIG. 8. At block 904, the method 900 includes recording data related to a first measurement of a two-dimensional acoustic field of the beam as the beam crosses a transverse plane of the array. In some embodiments, the two-dimensional acoustic field includes an acoustic pressure magnitude and a phase of the emitted beam At block 906, the method 900 includes measuring a first hologram of the emitted beam after the beam crossed the transverse plane. In some embodiments, the method 900 includes making a radiation force balance measurement of the source using a particular physical target. In some embodiments, making a radiation force balance measurement includes making a radiation force balance measurement under identical pulse waveform conditions as the hologram was measured. In further embodiments, the method 900 includes using the measured hologram to calculate a radiation force as a function of hydrophone sensitivity for the physical target used in the radiation force balance measurements.

At block 908, the method 900 includes using the recorded data of the first measured hologram to calculate a first characteristic of the two-dimensional acoustic field. In some embodiments, calculating the first characteristic includes calculating a hydrophone sensitivity by equating the radiation force balance measurement with the radiation force calculation based on the measured hologram.

At block 910, the method 900 includes adjusting a first parameter of the beam based on the first calculated characteristic of the two-dimensional acoustic field to emit a first calibrated beam. In some embodiments, after the parameter of the beam is adjusted, the method further includes emitting the first calibrated beam towards the array, recording data related to a second measurement of a two-dimensional acoustic field of the beam as the beam crosses the transverse plane of the array, measuring a second hologram of the emitted beam after the beam crossed transverse plane, using the recorded data of the second measurement and second measured hologram to calculate a second characteristic of the two-dimensional acoustic field, and adjusting a second parameter of the beam based on the second calculated characteristic of the two-dimensional acoustic field to emit a second calibrated beam.

In some embodiments, processing the measured hologram to reconstruct a characteristic of the ultrasound source includes determining at least one of an acoustic output power of the ultrasound source or a radiation force that would occur if an acoustic beam from the ultrasound source impinged on a particular target. In a particular embodiment, for example, the radiation force can be used in conjunction with an independent radiation force balance measurement to calibrate a hydrophone's sensitivity at a single frequency.

From the foregoing, it will be appreciated that specific embodiments of the technology have been described herein for purposes of illustration, but that various modifications may be made without deviating from the disclosure. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

III. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of measuring at least one characteristic of an ultrasound source using an array-based acoustic holography system, the method comprising:
    emitting a beam from an ultrasound source towards the array;
    as the beam crosses a plane of the array, capturing waveform measurements of the beam with a plurality of elongated elements disposed on a surface of the array, wherein the individual elongated elements are sized and shaped to have a first dimension larger than a width of the beam emitted by the ultrasound source toward the array;
    defining a measured hologram at the array surface based, at least in part, on the waveform measurements; and
    processing the measured hologram to reconstruct a characteristic of the ultrasound source.

2. The method of claim 1 wherein emitting a beam comprises emitting the beam having a beam characteristic based, at least in part, on one or more holography measurement parameters.

3. The method of claim 2 wherein an amplitude of excitation of the ultrasound source is from about 0.1 megahertz to about 10 megahertz.

4. The method of claim 1 wherein processing the measured hologram to reconstruct at least one characteristic of the ultrasound source comprises reconstructing one or more two-dimensional acoustic field characteristics of the ultrasound source, and wherein the two-dimensional acoustic field characteristics include acoustic pressure magnitude and phase.

5. The method of claim 1 wherein processing the measured hologram to reconstruct the characteristic of the ultrasound source comprises using the hologram to define a boundary condition of the ultrasound source.

6. The method of claim 1 wherein processing the measured hologram to reconstruct the characteristic of the ultrasound source comprises determining at least one of an acoustic output power of the ultrasound source or a radiation force that would occur if an acoustic beam from the ultrasound source impinged on a particular physical target.

7. The method of claim 2 wherein the one or more holography measurement parameters are a size of a hydrophone sensing region, a hydrophone bandwidth, or a reference position relative to a transducer at which the hydrophone is initially located.

8. The method of claim 1 wherein capturing waveform measurements of the beam with the plurality of elongated elements comprises capturing waveform measurements of the beam crossing the plane of the array and scanning two or more elongated elements of the plurality, wherein at least one element has a convex shape, a concave shape, or a flat shape, and wherein each element of the plurality has a length larger than a width of the acoustic beam.

9. The method of claim 1 wherein capturing waveform measurements of the beam with the plurality of elongated elements comprises moving the ultrasound source relative to the array, moving the array relative to the ultrasound source, or moving both the ultrasound source and the array.

10. The method of claim 9 wherein the moving the array or moving both the ultrasound source and the array comprises moving the array or moving both the ultrasound source and the array either continuously or in stepwise fashion through linear or angular displacements.

11. The method of claim 10 wherein the stepwise movement comprises one or more steps, wherein each step is less than half of a wavelength of the acoustic beam, wherein the linear movement includes movement in a first direction perpendicular to a height of the array, and wherein the angular movement includes movement in a second direction angularly around a first axis or a second axis, the first axis parallel to the array surface and perpendicular to at least one element and the second axis perpendicular to the array surface.

12. A method for calibrating an ultrasound source, the method comprising:
recording data related to a first measurement of a two-dimensional acoustic field of a beam emitted from an uncalibrated ultrasound source as the beam crosses a plane of an array having multiple elongated elements, wherein the elongated elements have an aspect ratio such that at least one dimension of each elongated element is greater than a width of the emitted beam;
measuring a first hologram of the emitted beam after the beam crossed the plane;
using the recorded data of the first measurement and first measured hologram to calculate a first characteristic of the two-dimensional acoustic field; and
adjusting a first parameter of the beam based on the first calculated characteristic of the two-dimensional acoustic field to emit a first calibrated beam.

13. The method of claim 12 wherein the two-dimensional acoustic field includes an acoustic pressure magnitude and a phase of the emitted beam.

14. The method of claim 12 wherein, after the parameter of the beam is adjusted, the method further comprises,
emitting the first calibrated beam towards the array;
recording data related to a second measurement of a two-dimensional acoustic field of the beam as the beam crosses the plane of the array;
measuring a second hologram of the emitted beam after the beam crossed the plane;
using the recorded data of the second measurement and second measured hologram to calculate a second characteristic of the two-dimensional acoustic field; and
adjusting a second parameter of the beam based on the second calculated characteristic of the two-dimensional acoustic field to emit a second calibrated beam.

15. A holography system, comprising:
an ultrasound source; and
an array having a plurality of elongated elements disposed on a surface of the array,
wherein each element of the plurality of elongated elements is sized and shaped to have a first dimension that is larger than a width of an acoustic beam emitted by the ultrasound source toward the array.

16. The holography system of claim 15, further comprising:
a physical computer-readable storage medium having stored thereon, computer-executable instructions that, if executed by a computing system, cause the computing system to perform operations comprising—
determining one or more holography measurement parameters;
instructing the hologram sensor to measure one or more characteristics of the acoustic beam after the beam crosses the array surface; and
generating one or more reconstructions of the beam characteristic.

17. The holography system of claim 16 wherein the array is a one-dimensional linear array, wherein the array surface is concave, convex, or flat, and wherein the array is coupled to a multichannel electronic receiver.

18. The holography system of claim 16 wherein the array comprises about 100 to about 200 elongated elements, and wherein the plurality of elongated elements are piezoelectrically activated elongated elements.

19. The holography system of claim 16 wherein the first dimension is about 50 to about 100 millimeters.

20. The holography system of claim 16, further comprising a multiplexer wherein the system operates in the absence of a preamplifier.

21. The holography system of claim 16 wherein the array is a hologram sensor.

22. The holography system of claim 16 wherein each element of the plurality is sized and shaped to have a second dimension that is smaller than half of a wavelength of an ultrasound beam.

23. The holography system of claim 22 wherein the second dimension is about 0.75 mm when the beam wavelength is about 1 MHz.

* * * * *